(12) United States Patent
Chu

(10) Patent No.: US 7,876,436 B2
(45) Date of Patent: Jan. 25, 2011

(54) IRRADIATION UNIT FOR A FLOW-CYTOMETRY-BASED ANALYTICAL INSTRUMENT AND ANALYTICAL INSTRUMENT INCLUDING THE SAME

(75) Inventor: Jianjun Chu, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 195 days.

(21) Appl. No.: 11/932,847

(22) Filed: Oct. 31, 2007

(65) Prior Publication Data

US 2008/0186490 A1   Aug. 7, 2008

(30) Foreign Application Priority Data

Feb. 2, 2007   (CN) .................. 2007 1 0073186

(51) Int. Cl.
*G01N 21/00* (2006.01)
(52) U.S. Cl. ....................... 356/338; 356/336
(58) Field of Classification Search ............... 356/410, 356/335–343
See application file for complete search history.

(56) References Cited

U.S. PATENT DOCUMENTS

| | | | | |
|---|---|---|---|---|
| 3,476,463 | A * | 11/1969 | Kreuzer | 359/717 |
| 4,327,972 | A * | 5/1982 | Brunsting | 362/335 |
| 4,850,707 | A | 7/1989 | Bowen et al. | |
| 4,990,795 | A * | 2/1991 | Suzuki et al. | 250/574 |
| 5,331,468 | A * | 7/1994 | Noethen | 359/738 |
| 5,891,734 | A * | 4/1999 | Gill et al. | 436/43 |
| 5,999,256 | A * | 12/1999 | Jones et al. | 356/335 |
| 2002/0167751 | A1 * | 11/2002 | Lee et al. | 360/72.1 |
| 2004/0196456 | A1 * | 10/2004 | Stern et al. | 356/317 |

(Continued)

FOREIGN PATENT DOCUMENTS

CN        1025078        6/1994

(Continued)

OTHER PUBLICATIONS

Yas, Alsultanny, Laser beam analysis using image processing, Jan. 2006, Journal of Computer Science, 109-113, pp. 109-112.*

(Continued)

*Primary Examiner*—Tarifur Chowdhury
*Assistant Examiner*—Michael LaPage
(74) *Attorney, Agent, or Firm*—Vista IP Law Group, LLP.

(57) ABSTRACT

Disclosed is an irradiation unit for a flow-cytometry-based analytical instrument and analytical instrument including the same. The irradiation unit includes a light source, a light beam focusing module for focusing the illuminating light beam on an irradiated area, and a light beam shaper disposed between the light source and the light beam focusing module. The light shaper is used for flattening the distribution of light intensity on the irradiated area in a third direction X that is perpendicular to both a first direction in which the light beam spreads and a second direction in which cells to be detected flow. The irradiation unit and the analytical instrument including the same enable the illuminating light beam to form the irradiated area with the uniform distribution of intensity in a predetermined direction to avoid misjudging particles of the same kind entering into different positions of the irradiated area as different, thereby improving accuracy.

20 Claims, 9 Drawing Sheets

U.S. PATENT DOCUMENTS

2005/0110996 A1* 5/2005 Sharpe et al. .............. 356/338
2006/0192940 A1 8/2006 Phi-Watson

FOREIGN PATENT DOCUMENTS

| CN | 1116708 | 2/1996 |
| CN | 1529830 | 9/2004 |
| CN | 1200111 | 5/2005 |
| CN | 1224936 | 10/2005 |

OTHER PUBLICATIONS

"The Designation and Experiment of the DOE Applied to Shape the Laser Beam to Square Frame Shape". Laser Technology, vol. 29, No. 2; Apr. 2005.
High Power Laser and Particle Beams; vol. 17, No. S0; Apr. 2005.
Search Report dated Jul. 16, 2007 for Chinese Patent Application No. 200710073186.3

* cited by examiner

IRRADIATION UNIT FOR A FLOW-CYTOMETRY-BASED ANALYTICAL INSTRUMENT AND ANALYTICAL INSTRUMENT INCLUDING THE SAME

STATEMENT OF RELATED APPLICATION

The present application claims priority of the Chinese Patent Application No. 200710073186.3, entitled "Photosensor for A Flow-Cytometry-Based Instrument and Irradiation Unit thereof", filed on Feb. 2, 2007, which is incorporated herein by reference in its entirety.

FIELD OF THE INVENTION

The present invention relates to a flow-cytometry-based analytical instrument, in particular to an irradiation unit for a flow-cytometry-based analytical instrument and an analytical instrument including the same.

BACKGROUND OF THE INVENTION

A flow-cytometry-based analytical instrument comprises a flow cytometer, a blood analyzer, a urine analyzer or a particle analyzer etc, and utilizes a photosensor to collect and analyze two-dimensional or multi-dimensional optical signals from particles so as to identify different particles in the liquid for classification. As shown in FIGS. 1a and 1b, the existent flow-cytometry-based analytical instrument ordinarily comprises an illumination unit 1, a flow chamber 2 and a photo-detection unit (not shown), in which the illumination unit 1 generally consists of a light source 11 and a light beam focusing module 13. The illumination unit 1 is arranged to provide an irradiating light beam, which is projected into a through hole 21 in the flow chamber 2 to form an irradiated area for detection after being shaped by the light beam focusing module 13. When cells flow through the irradiated area, the irradiating beam irradiates cells to cause scattering or initiate fluorescence emission etc, wherein the direction in which cells flow is defined as Y direction, that in which the light beam spreads is defined as Z direction, and that simultaneously perpendicular to both directions in which cells flow and the light beam spreads is defined as X direction. The light beam focusing module can focus Gauss light beams from the light source 11 into the irradiated area which is equal in size to that of a cell in Y direction and to that of the inner wall of the through hole 21 in the flow chamber 2 in X direction, wherein light energy is highly concentrated. Thus, when cells pass through this area, a scattered signal and a fluorescence signal in rather great intensity are easily formed for receiving by the photodetection unit.

The flow chamber 2 is provided with a through hole 21 through which cells can flow, and in which the cells are encased into the sheath fluid based on the fluid focusing principle such that the cells can pass through the irradiated area one by one. In the irradiated area, particles will generate different optical signals as irradiated by the laser light, such as a forward scattered signal (FSC), a side scattered signal (SSC) and a multipath fluorescence signal (FL) etc.

The photodetection unit is disposed to collect a variety of optical signals generated in the flow chamber 2 and convert them into electrical signals, and then transmit these electrical signals to subsequent analytical systems for processing and analyzing to obtain parameters of various cells existent in the fluid, thereby processing accounting and classifying, etc.

In the prior art, the methods are all concerned with using two mutually perpendicular cylindrical lenses to focus the emitted light beam into an elliptical spot to irradiate cells. The Gauss light beams converge at the through hole 21 in the flow chamber 2 in X direction through one cylindrical lens and near the flow chamber 2 in Y direction through the other cylindrical lens. As shown in FIG. 2, the spot in the flow chamber is elliptical, and is approximately equal in size to the cell diameter in Y direction and to that of the inner wall of the through hole 21 in the flow chamber 2 in X direction, and the optical field distribution in X and Y directions is substantially the Gauss distribution.

In the prior art, only the size of the irradiated spot are considered in use of a set of cylindrical lenses to focus the Gauss light beams, without taking the distribution of light intensity in different directions into account. As the use of cylindrical lenses cannot realize the "flat-top" distribution of light intensity, the light intensity in X and Y directions is still presented in the Gauss distribution. Thus, when particles of the same kind pass through different positions of this irradiated area, scattering signals or fluorescence signals in different intensity are formed due to different light intensity irradiated thereon, thereby rendering a misjudgment on the particle. Said misjudgment can be explained via FIGS. 3 and 4. FIG. 3 shows the shape of the irradiated spot and the distribution of light intensity in X direction, in which particles A and B of the same kind enter different positions of an irradiated area 3, and light energy irradiated on particle A in the center of the spot is different from that on particle B away from the center of the spot due to non-uniformity of the distribution of light intensity. As shown in FIG. 4, that will render particle A in the center of the spot and particle B away from the center of the spot to respectively form different scattering signals, i.e. respectively form scattering signal A and scattering signal B. Then, subsequent analytical modules are likely to determine particle B different from particle A based on the scattering signals, thereby causing an error.

SUMMARY OF THE INVENTION

The technical problem to be solved in the present invention is to overcome the shortcomings in the prior art, and there is provided an irradiation unit for a flow-cytometry-based analytical instrument, which can realize the uniform distribution of the light beam irradiating cells in a direction that is perpendicular to both directions in which cells flow and the light beam spreads.

Another technical problem to be solved in the present invention is to provide a flow-cytometry-based analytical instrument including the irradiation unit, capable of realizing the uniform distribution of the light beam irradiating cells in the direction that is perpendicular to both directions in which cells flow and the light beam spreads, so as to eliminate the errors occurring when cells enter different positions of the irradiated area.

According to the first aspect of embodiments of the present invention, there is provided an irradiation unit for a flow-cytometry-based analytical instrument, comprising a light source for emitting an illuminating light beam; a light beam focusing module for focusing the illuminating light beam into an irradiated area; and a light beam shaper disposed between the light source and the light beam focusing module, for flattening the distribution of light intensity on the irradiated area in the direction that is perpendicular to both directions in which cells to be detected flow and the light beam spreads.

Preferably, the light source is a laser source, which comprises at least two lasers emitting Gauss light beams with different characteristics. The light beam shaper is a diffractive optical element. Further preferably, the diffractive optical element is a one-dimensional diffractive optical element, for flattening the distribution of light intensity in the irradiated area in the direction that is perpendicular to both directions in which cells flow and the light beam spreads. A factor β of the light beam shaper satisfies the following formula:

$$\beta = \frac{2\sqrt{2\pi}\,\omega_0 y_0}{\lambda d} \geq 40,$$

wherein $\omega_0$ is the waist radius of Gauss light beams; $y_0$ is the half width of the shaped spot; $\lambda$ is the wavelength of the incident light beam; and d is a distance from the light beam shaper to a shaping plane.

Further preferably, the light beam focusing module comprises a focusing lens for focusing the light beam in the direction in which cells flow, wherein the focus point of focusing lenses is in the center of the irradiated area, and at least two cylindrical lenses for compressing and magnifying the light beam in the direction that is perpendicular to both directions in which cells flow and the light beam spreads.

Also preferably, the irradiated area is equal in size to the cell diameter in the direction in which cells flow and to that of the inner wall of the through hole in the flow chamber through which cells to be detected pass in the direction that is perpendicular to both directions in which cells flow and the light beam spreads.

According to the second aspect of embodiments of the present invention, there is provided a flow-cytometry-based analytical instrument, comprising a light source for emitting an illuminating light beam; a light beam focusing module for focusing the illuminating light beam on the irradiated area; a light beam shaper disposed between the light source and the light beam focusing module, for flattening the distribution of light intensity in the irradiated area in the direction that is perpendicular to both directions in which cells to be detected flow and the light beam spreads; a flow chamber for enabling cell flows encased in the sheath fluid to pass through the irradiated area one by one; and a photodetection unit for collecting the optical information from cells passing through the flow chamber and irradiated by the light beam, and converting the optical information into electrical signals.

Preferably, the light source is a laser source, which comprises at least two lasers emitting Gauss light beams with different characteristics. The light beam shaper is a diffractive optical element. Further preferably, the diffractive optical element is a one-dimensional diffractive optical element for flattening the distribution of light intensity in the irradiated area in the direction that is perpendicular to both directions in which cells flow and the light beam spreads. A factor β of the light beam shaper satisfies the following formula:

$$\beta = \frac{2\sqrt{2\pi}\,\omega_0 y_0}{\lambda d} \geq 40,$$

wherein $\omega_0$ is the waist radius of Gauss light beams; $y_0$ is the half width of the shaped spot; $\lambda$ is the wavelength of the incident light beam; and d is a distance from the light beam shaper to a shaping plane.

Further preferably, the light beam focusing module comprises a focusing lens for focusing the light beam in the direction in which cells flow, wherein the focus point of focusing lens is in the center of the irradiated area, and at least two cylindrical lenses for compressing and magnifying the light beam in the direction that is perpendicular to both directions in which cells flow and the light beam spreads.

Also preferably, the light beam focusing module forms in the flow chamber an irradiated area which is equal in size to the cell diameter in the direction in which cells flow and to that of the inner wall of the through hole in the flow chamber in the direction that is perpendicular to both directions in which cells flow and the light beam spreads.

The advantages of the present invention over the prior art lie in following two aspects. Firstly, the irradiation unit for the flow-cytometry-based analytical instrument according to the embodiments of the present invention can enable the irradiating light beam to form in the flow chamber an irradiated area with the uniform distribution of light intensity in the direction that is perpendicular to both directions in which cells flow and the light beam spreads. Thus, when cells or particles of the same kind enter different positions of the irradiated area, the optical signals with substantially equal intensity can be obtained such that subsequent analytical modules will refrain from misjudging said particles of the same kind as different so as to avoid the errors, thereby facilitating a system to identify particles and improving the stability. Secondly, the accuracy of the flow-cytometry-based analytical instrument including the irradiation unit according to the embodiments of the present invention has been improved greatly, and therefore the requirement on the stability of fluid can be reduced significantly, and then the difficulty in manufacturing the flow-cytometry-based analytical instrument is reduced.

BRIEF DESCRIPTION OF THE DRAWINGS

FIGS. 5a and 5b are block diagrams of an analytical instrument according to the embodiments of the present invention, in which FIG. 5a is a top view and FIG. 5b is a side view;

DETAILED DESCRIPTION OF THE INVENTION

Figure 1A:
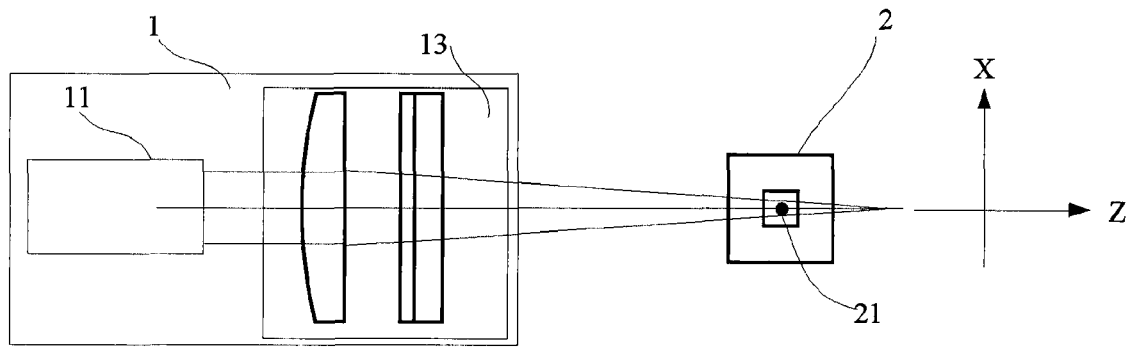
FIGS. 1a and 1b are block diagrams illustrating a flow-cytometry-based analytical instrument in the prior art.
Figure 1B:
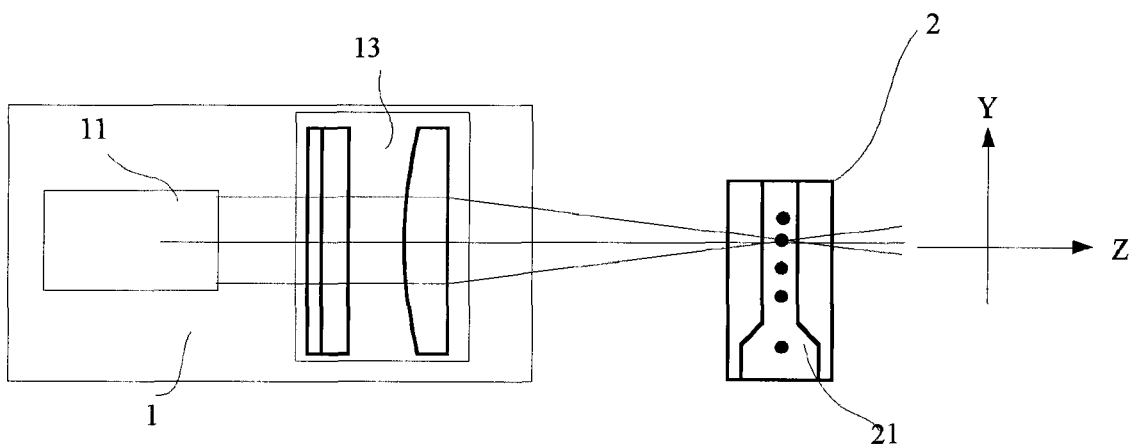
Figure 2:
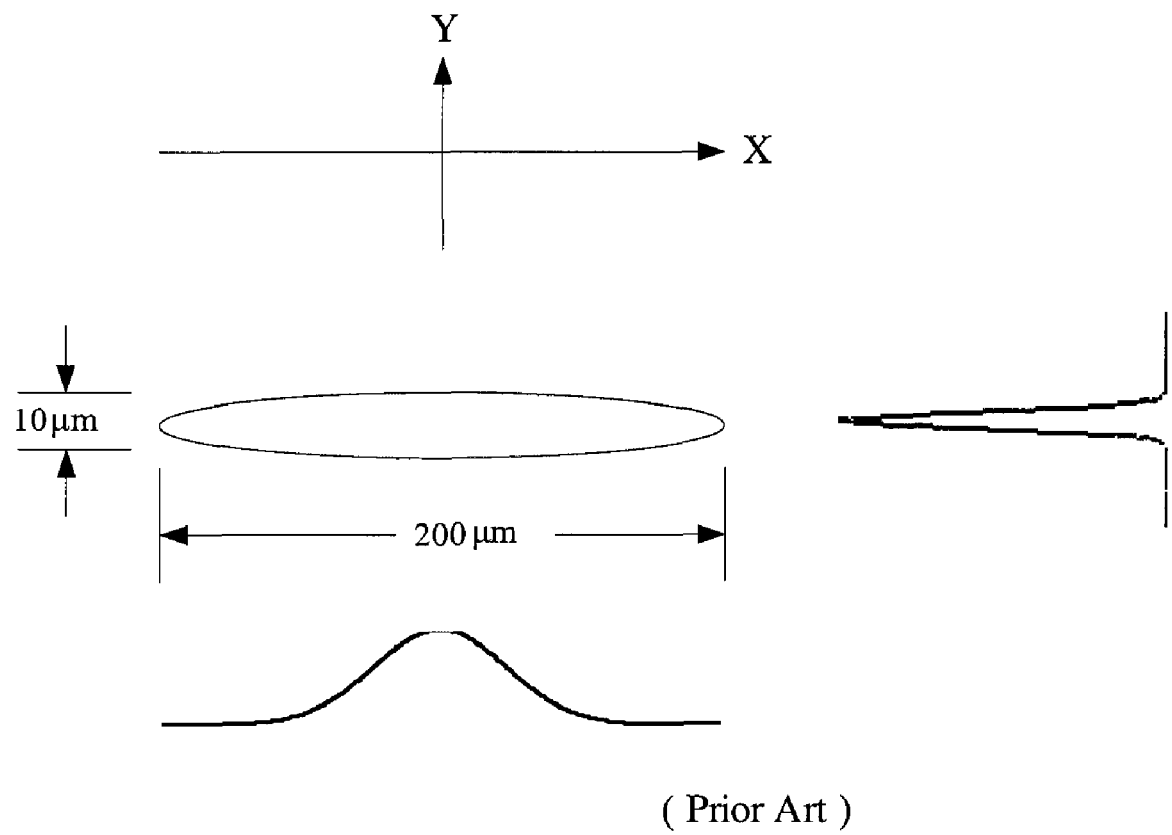
FIG. 2 is a schematic diagram illustrating the shape of an irradiated spot and the optical field distribution formed by an irradiation unit in the prior art.
Figure 3:
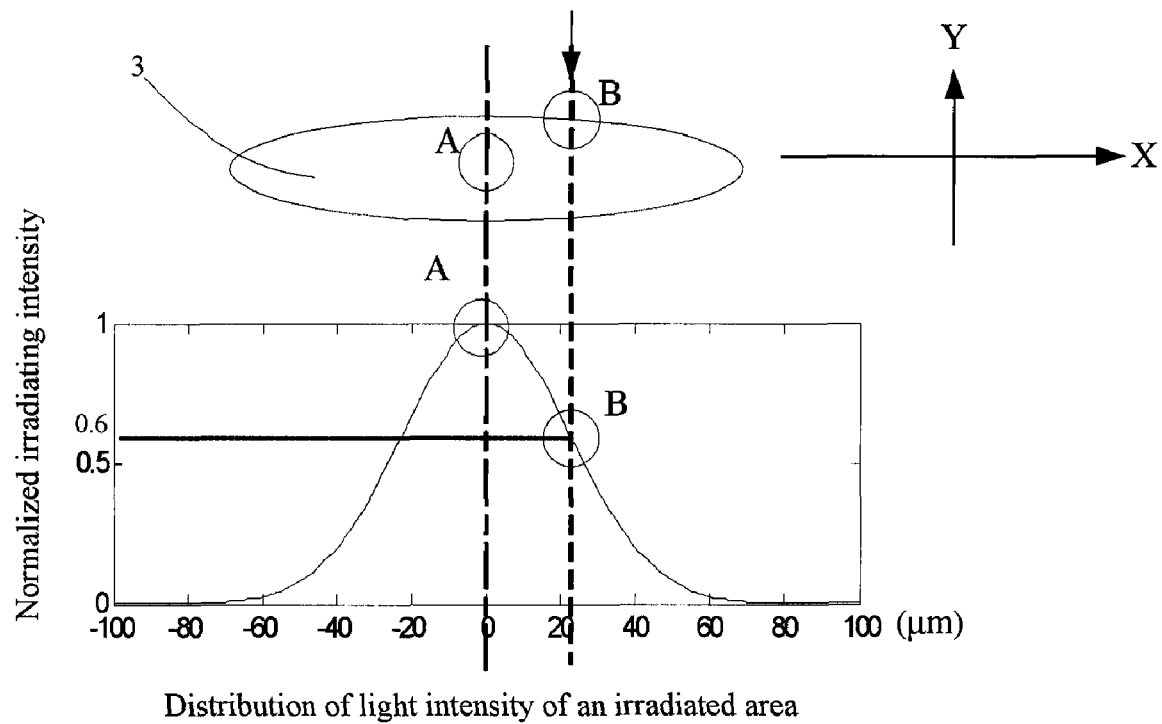
FIG. 3 is a schematic diagram illustrating the shape of the irradiated spot and the distribution of light intensity in X direction in the prior art.
Figure 4:
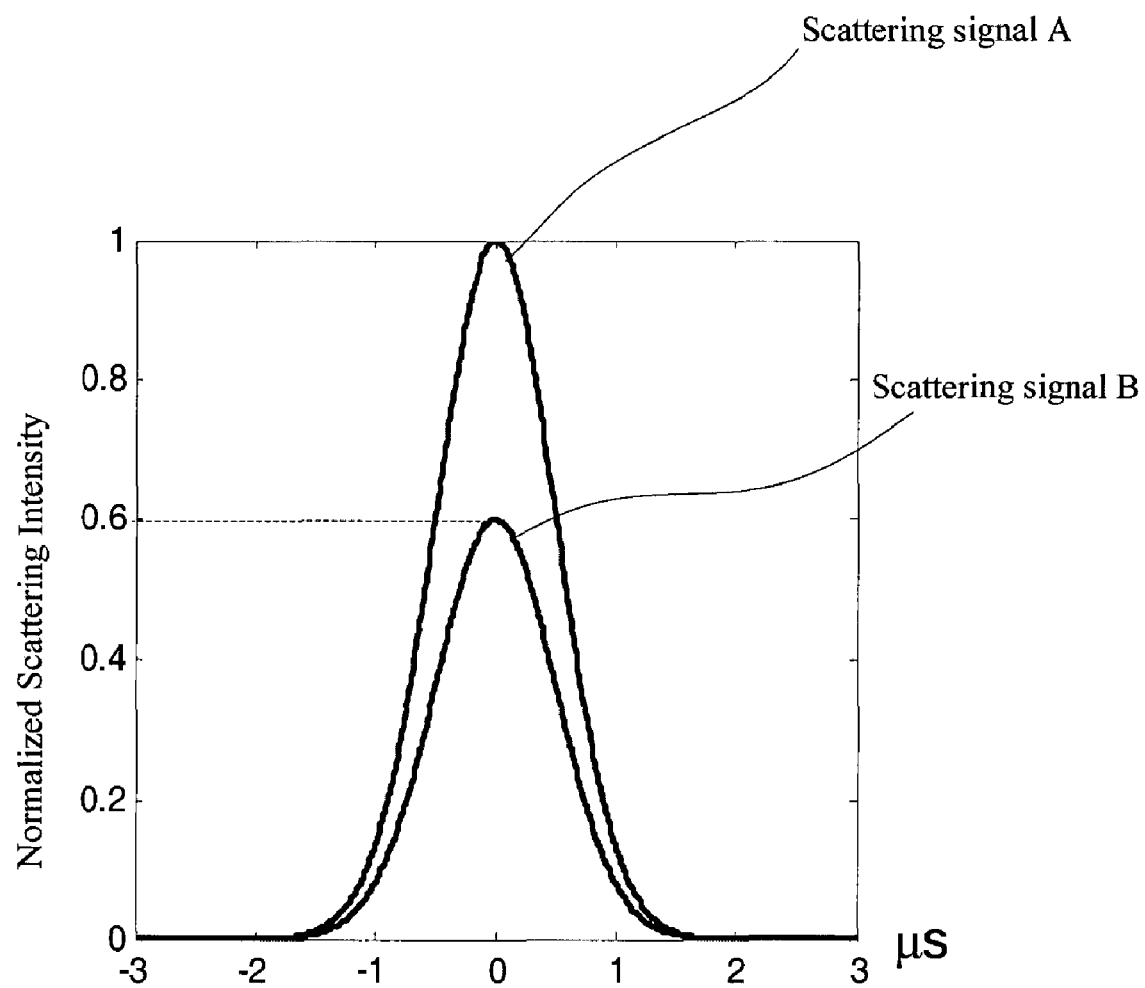
FIG. 4 is a schematic diagram of optical signals formed when particles of the same kind enter into different positions of an irradiated area in the prior art.
Figure 5A:
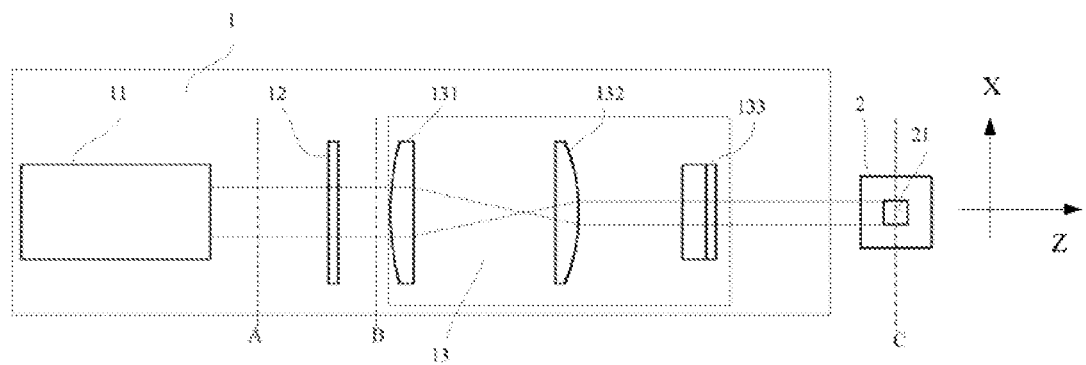
Figure 5B:
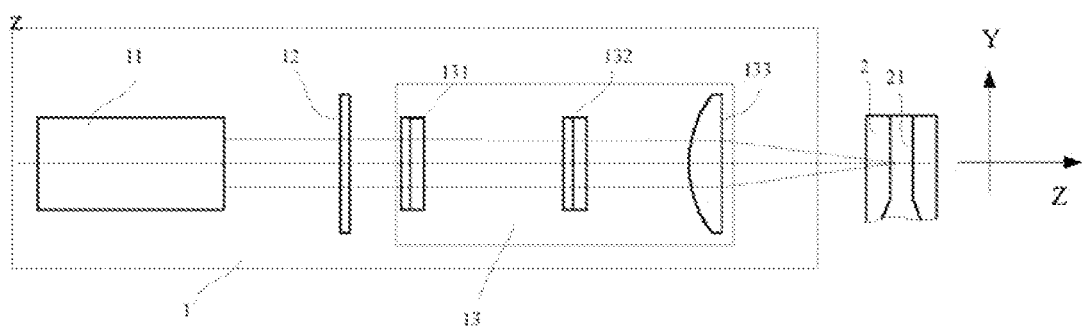

FIGS. 5a and 5b show a flow-cytometry-based analytical instrument, comprising an irradiation unit 1, a flow chamber 2 and a photodetection unit (not shown). The irradiation unit 1 consists of a light source 11, a light beam shaper 12 and a light beam focusing module 13 which are arranged sequentially. The flow chamber 2 includes a through hole 21, through which cells encased in the sheath fluid based on the fluid focusing principles can flow.

The light source 11 may be a laser emitting Gauss light beams with one kind of characteristic, or may comprise at least two lasers emitting Gauss light beams with different characteristics. In this embodiment, the light source 11 is preferably the latter, as the light beam emitted from the light source 11 is basic-mode Gauss light beams, and the distribution of the intensity on the cross section is circularly symmetrical Gauss distribution. The analytic expression for Gauss light beams spreading along Axis Z is as follows:

$$E(x, y, z) = E_0 \frac{\omega_0}{\omega(z)} e^{-\frac{x^2+y^2}{\omega^2(z)}} e^{-i\left\{k\left[z+\frac{x^2+y^2}{2R(z)}\right]-tg^{-1}\frac{z}{f}\right\}},$$

$$\begin{cases} \omega(z) = \omega_0 \sqrt{1 + \left(\frac{z}{f}\right)^2} \\ R(z) = z + \frac{f^2}{z}, \end{cases}$$

wherein the origin point of Axis Z is set at the waist of the light beam; R(z) and ω(z) respectively represent the radius of the equiphase surface curvature and the spot radius on equiphase surface of Gauss light beams at Coordinate Z; $\omega_0$ is the waist radius of Gauss light beams; f is the confocal cavity parameter for generating Gauss light beams, also known as the focal parameter of Gauss light beams. The relation between $\omega_0$ and f is:

$$f = \frac{\pi \omega_0^2}{\lambda},$$

$$\text{wherein } \omega_0 = \sqrt{\frac{\lambda f}{\pi}}.$$

The light beam shaper 12 is used to shape the light beam emitted from the light source 11, such that the intensity in X direction is in uniform distribution. As shaping is performed only in X direction, the light beam in Y direction is still in Gauss distribution. The light beam shaper 12 may be a set of aspherical lenses or a graded index lens (GRIN) or a diffractive optical element, wherein the diffractive optical element can simultaneously shape a variety of Gauss light beams with different characteristics without unfavorably influencing effects of shaping. Additionally, the diffractive optical element is a one-dimensional diffractive optical element for flattening the optical field distribution only in X direction.

Figure 6A:
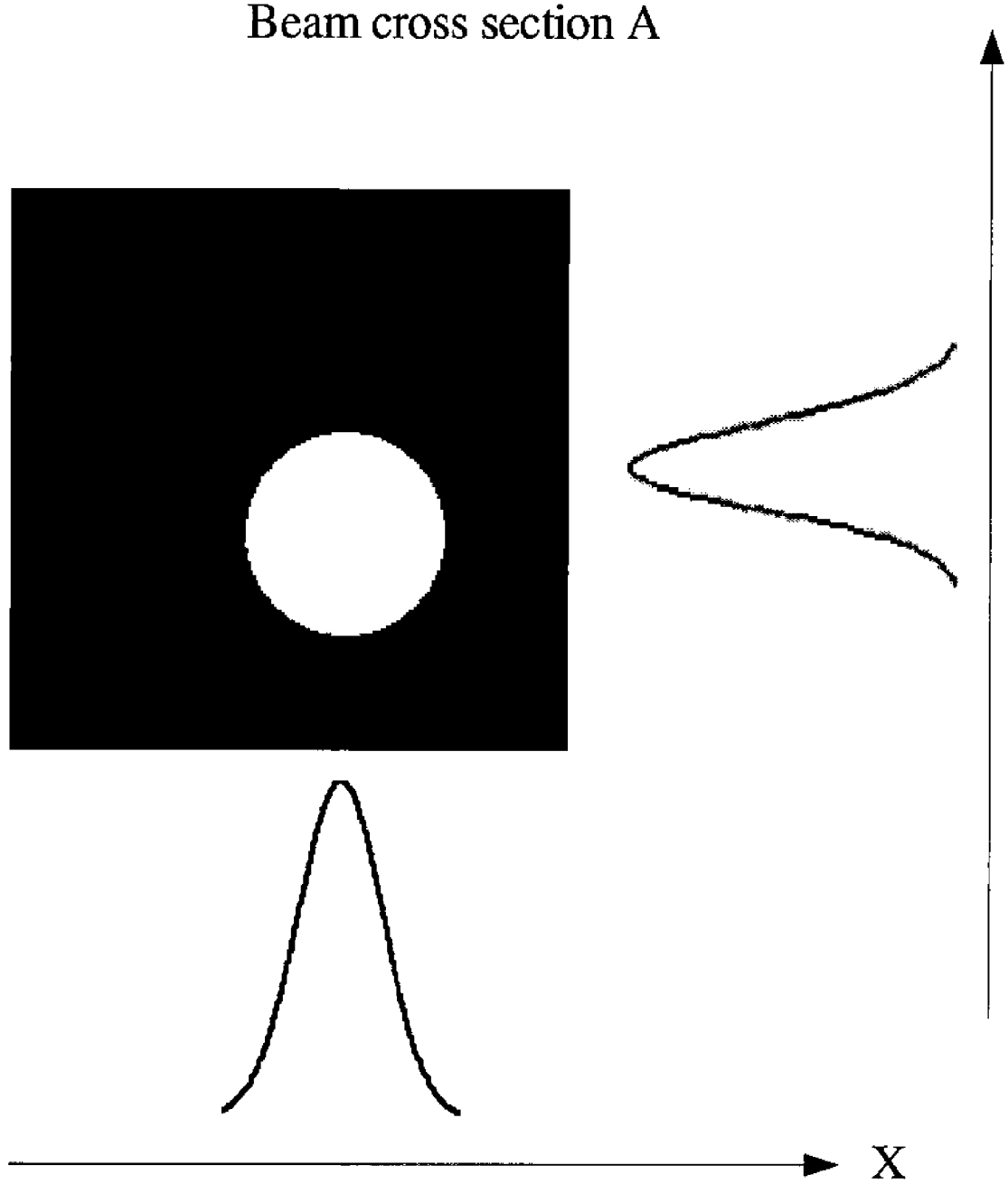
FIG. 6a is a schematic diagram illustrating the shape of beam cross-section and the distribution of optical field before being shaped.
Figure 6B:
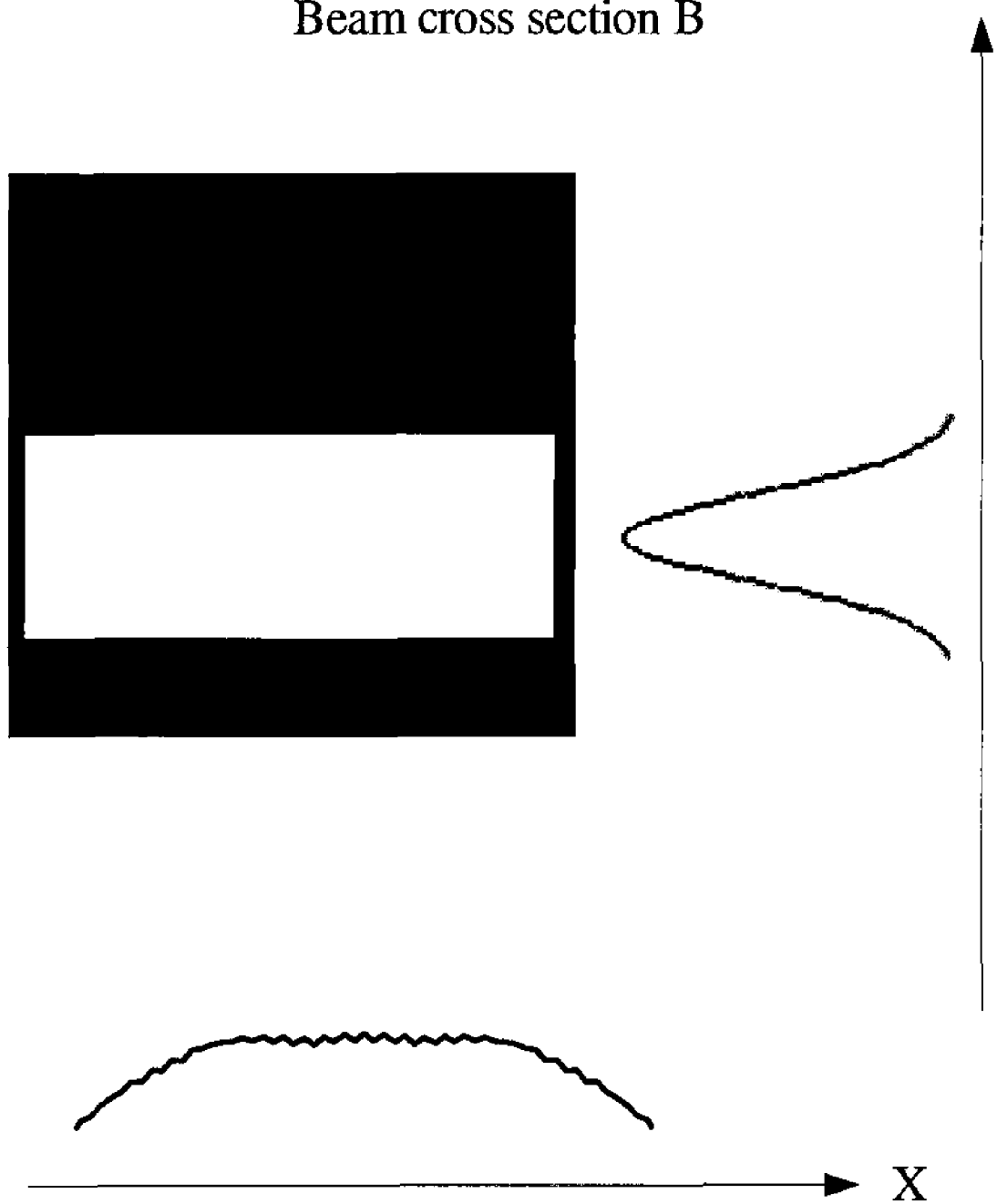
FIG. 6b is a schematic diagram illustrating the shape of beam cross-section and the distribution of optical field after being shaped.

FIG. 6a shows the optical field distribution and the shape of the light beam cross-section A before the light beam shaper 12 shapes the light beam. As shown in FIG. 6a, before the light beams enter the light beam shaper 12, their optical fields in X and Y directions are all in Gauss distribution. FIG. 6b shows the shape of the light beam cross-section B and the optical field distribution after the light beam shaper 12 shapes the light beam, wherein the optical field of the shaped light beam in Y direction is still in Gauss distribution, but in X direction becomes substantially uniform.

The light beam focusing module 13 is used to compress the shaped light beam respectively in mutually perpendicular X and Y directions such that an irradiated area of a predetermined size can be formed when the irradiating light beam reaches the flow chamber 2. The predetermined size is substantially equal to the cell diameter in Y direction and to the size of the inner wall of the through hole 21 in the flow chamber 2 in X direction. The light beam focusing module 13 is preferably a set of lenses, in which the entrance pupil position of the set of lenses coincides with the flat field plane and the exit pupil position is at the flow chamber, i.e. the position where cells are irradiated.

The set of lenses comprises a first cylindrical lens 131 and a second cylindrical lens 132 disposed to compress and magnify the light beam in X direction, and a one-dimensional focusing lens 133 focusing the light beam in Y direction. The one-dimensional focusing lens 133 is preferably a cylindrical lens, of which the focal point is arranged in the center of the flow chamber to maintain X and Y directions confocal.

The design for the light beam shaper 12 is constrained by a factor β, which can be expressed as:

$$\beta = \frac{2\sqrt{2\pi} \, \omega_0 y_0}{\lambda d},$$

wherein $\omega_0$ is the waist radius of Gauss light beams; $y_0$ is the half width of the shaped spot; λ is the wavelength of the incident light beam; and d is a distance from the light beam shaper to a shaping plane.

According to uncertainty principle, β should be higher than 0.69. The higher the β value, the steeper the distribution of the shaped light beam at the edge, but meanwhile the flutter at the edge is more severe; and the lower the β value, the worse the effects of the flat field distribution of the shaped light beam, but the distribution near the edge is smoother. The specific range of β value is selected according to the acceptable extent of the flat-top range and the flutter at the edge by the system. In a flow cytometer, in order to obtain a wide range of the flat field distribution, β value should be as high as possible and preferably is β≧40.

In the definition of the factor β, $\omega_0$ and λ are characteristics of the incident light beam, which are fixed values. On account of configuration constraint of the system, d cannot be very small. If a higher β value is required, the half width $y_0$ of the shaped spot must be increased properly. However, according to the features of the flow cytometer, the width of the irradiated spot in X direction should be equal to that of the inner wall of the flow chamber which in general is approximately between 200 μm and 400 μm in the flow cytometer. Use of two cylindrical lenses capable of compressing and magnifying the light beam in X direction enable the size of the irradiated spot, in X direction, of the light beam shaped by the light beam shaper to satisfy the requirement on the size of the inner wall of the flow chamber when β value of the light beam shaper 12 is relatively high.

The light beam shaped by the light beam shaper 12 has no changes in the size thereof in Y direction. However, the one-dimensional focusing lens 133 compress the size of the spot in Y direction such that the irradiating light beam in Y direction, when it reached the center of the flow chamber, is equal in size to the cell diameter which is generally about 10 μm. As it is not necessary to be uniform in the distribution of light intensity in Y direction, the optical field distribution in Y direction is always in Gauss distribution.

Figure 7:
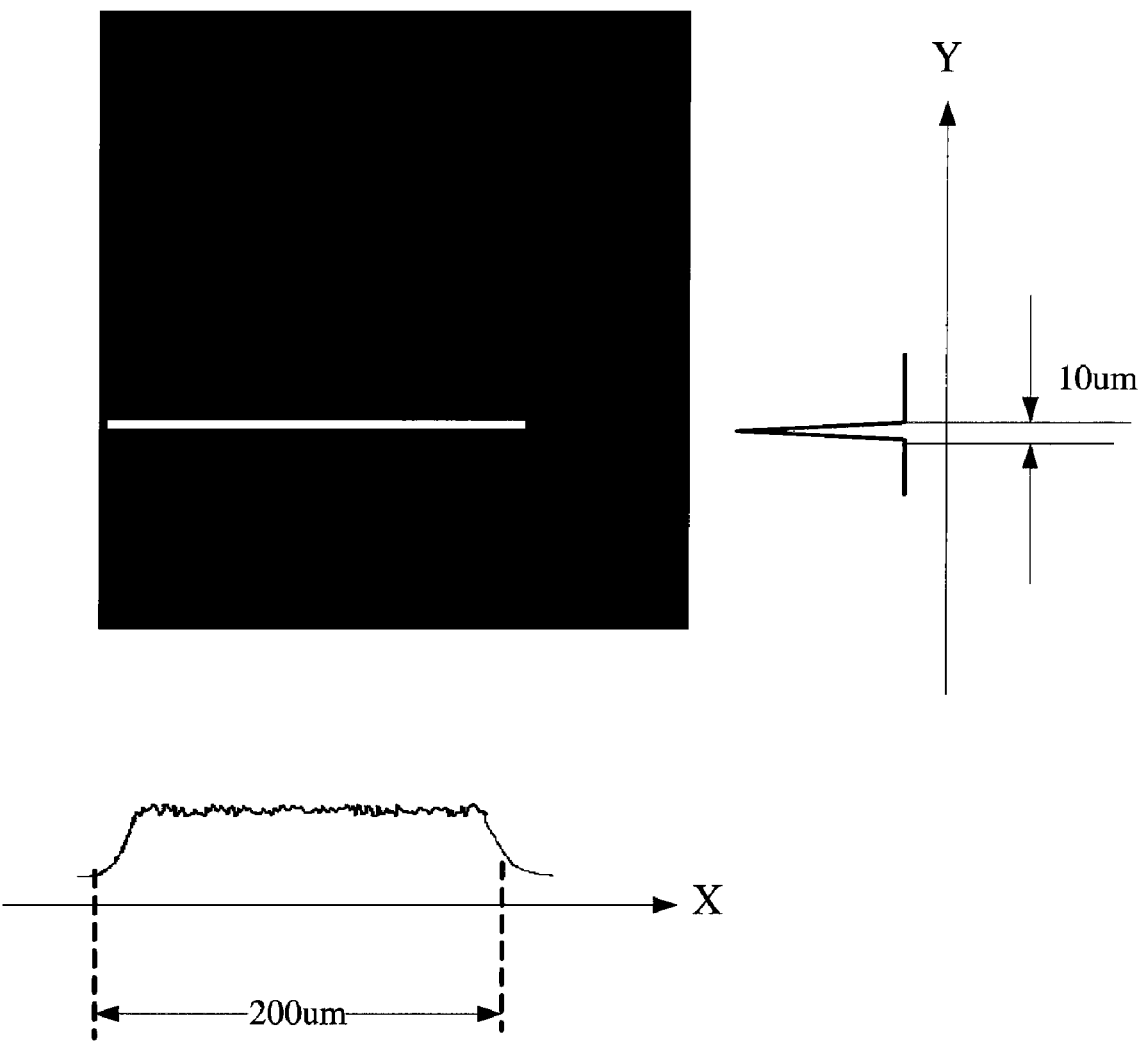
FIG. 7 is a schematic diagram illustrating the distribution of light intensity of an irradiated area irradiated on cells.

The shaped light beam converge in the center of the flow chamber after passing through the light beam focusing module 13, with the distribution thereof as shown in FIG. 7: a flat field distribution of about 200 μm in X direction and the Gauss distribution of about 10 μm in Y direction are formed.

Figure 8:
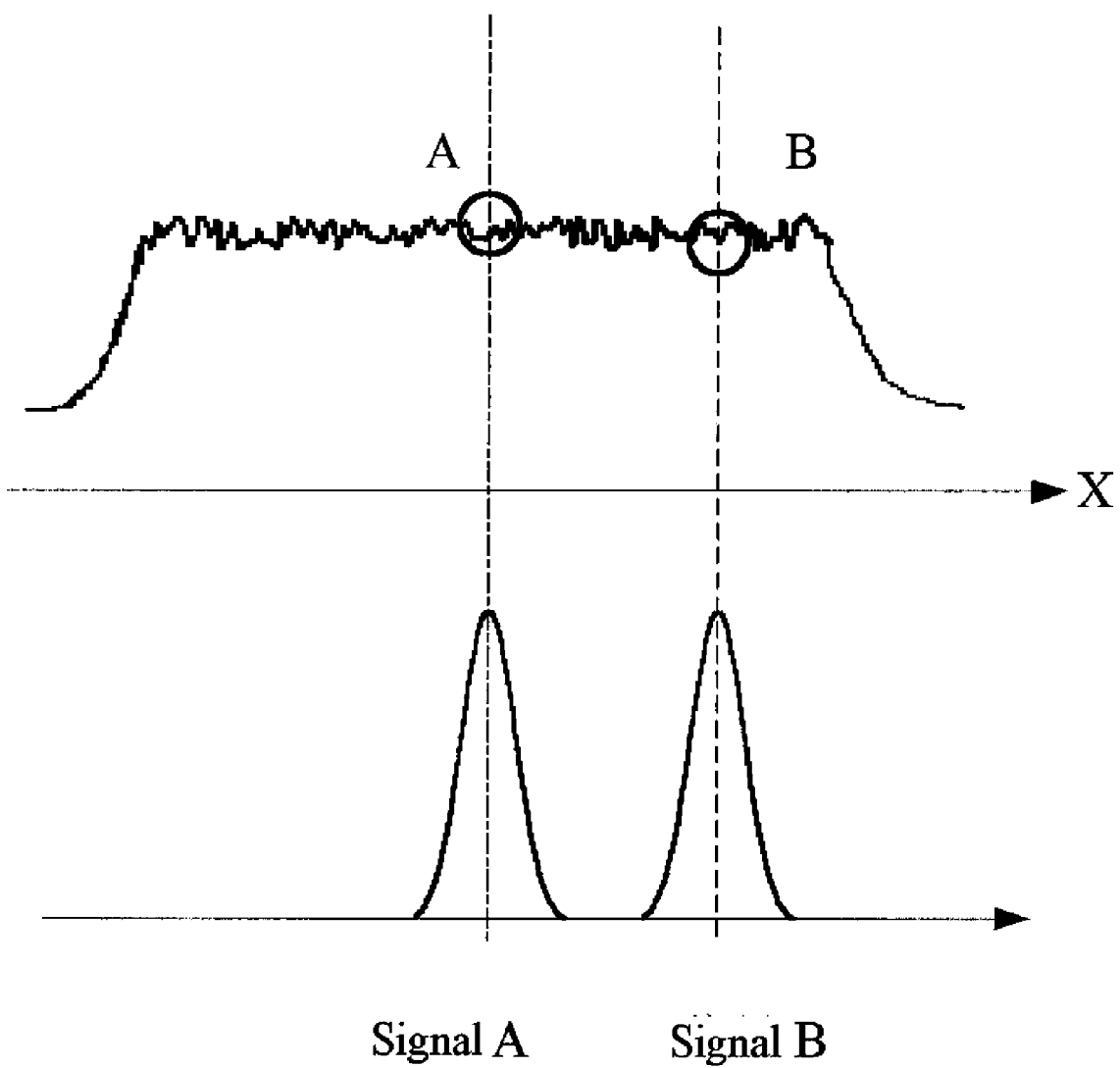
FIG. 8 is a schematic diagram of optical signals formed when particles of the same kind enter into different positions of the irradiated area according to the embodiments of the present invention.

As shown in FIG. 8, when particles A and B of the same kind enter the irradiated area from different positions, signals of the same intensity can be obtained, i.e. a scattered signal and a fluorescence signal of the same amplitude can be obtained.

Cell flows encased in the sheath fluid pass through the irradiated area in the flow chamber 2 one by one and form a variety of optical information after being irradiated. The flow chamber 2 is made of transparent material, generally quartz, and the inner wall of the through hole 21 thereof is square or rectangular.

The photodetection unit is used to collect optical information from cells and convert the optical information into electrical signals, and it can be implemented in various ways of the prior art, which will not be described in detail herein. The photodetection unit can also magnify the electrical signals and usually comprises a photodiode and a photomultiplier etc.

The present invention has been described in detail by way of above-mentioned specific preferred embodiments, but the present invention is not construed to be limiting to these embodiments. For a person skilled in the art, simple inference or substitution can be made to the invention without departing from the conception of the present invention, which should be within the protection scope of the present invention.

The invention claimed is:

1. An irradiation unit for a flow-cytometry-based analytical instrument, comprising:
   a light source for emitting an illuminating light beam in a first direction Z;
   a light beam focusing module for focusing the illuminating light beam on an irradiated area, wherein
      the irradiated area comprises an area through which cells to be detected flow in a second direction Y; and
   a light beam shaper disposed between the light source and the light beam focusing module and configured for flattening distribution of light intensity on the irradiated area along the second direction Y, in which the cells to be detected flow, wherein
      the light beam shaper is configured for flattening the distribution of the light intensity along the second direction Y but not along a third direction X that is perpendicular to the first direction Z and the second direction Y, and
      the light beam shaper is further configured for broadening the distribution of the light intensity in the second direction Y to expand a size of the irradiation area in the second direction Y to become larger than an original size of an original irradiation area that is irradiated by the light beam without the light beam shaper.

2. The irradiation unit according to claim 1, wherein
the light source comprises a laser source, which comprises at least two lasers emitting Gauss light beams with different characteristics; and
the light beam shaper is a diffractive optical element.

3. The irradiation unit according to claim 2, wherein
the diffractive optical element comprises a one-dimensional diffractive optical element for flattening the distribution of light intensity on the irradiated area along the second direction Y in which the cells flow, in which the second direction Y is perpendicular to the first direction Z and the third direction X.

4. The irradiation unit according to claim 1, wherein a factor $\beta$ of the light beam shaper satisfies the following formula:

$$\beta = \frac{2\sqrt{2\pi}\,\omega_0 y_0}{\lambda d} \geq 40,$$

in which $\omega_0$ is the waist radius of Gauss light beams; $y_0$ is the half width of a shaped spot; $\lambda$ is the wavelength of the incident light beam; and $d$ is a distance from the light beam shaper to a shaping plane.

5. The irradiation unit according to claim 1, wherein
the light beam focusing module comprises a focusing lens module for focusing the light beam in the second direction Y in which the cells flow, wherein a focus point of the focusing lens module is at a center of the irradiated area, and the focusing lens module comprising at least two cylindrical lenses for compressing and magnifying the light beam in the third direction X that is perpendicular to both the second direction Y in which the cells flow and the first direction Z in which the light beam spreads.

6. The irradiation unit according to claim 1, wherein
the irradiated area is equal in size to the cell diameter in the second direction Y in which the cells flow.

7. A flow-cytometry-based analytical instrument, comprising:
   a light source for emitting an illuminating light beam in a first direction Z;
   a light beam focusing module for focusing the illuminating light beam on an irradiated area, wherein the irradiated area comprises an area through which cells to be detected flow in a second direction Y;
   a light beam shaper disposed between the light source and the light beam focusing module and configured for flattening distribution of light intensity on the irradiated area along the second direction Y, in which the cells to be detected flow, wherein
      the light beam shaper is configured for flattening the distribution of the light intensity along the second direction Y but not along the third direction X, and
      the light beam shaper is further configured for broadening the distribution of the light intensity in the second direction Y to expand a size of the irradiation area in the second direction Y to become larger than an original size of an original irradiation area that is irradiated by the light beam without the light beam shaper;
   a flow chamber for enabling cell flows encased in a sheath fluid to pass through the irradiated area one by one; and
   a photodetection unit for collecting optical information from cells passing through the flow chamber and irradiated by the light beam, and converting the optical information into electrical signals.

8. The analytical instrument according to claim 7, wherein
the light source comprises a laser source, which comprises at least two lasers emitting Gauss light beams with different characteristics; and
the light beam shaper is a diffractive optical element.

9. The analytical instrument according to claim 8, wherein
the diffractive optical element comprises a one-dimensional diffractive optical element for flattening the distribution of light intensity on the irradiated area along the second direction Y that is perpendicular to both the third direction X and the first direction Z.

10. The analytical instrument according to claim 7, wherein
a factor $\beta$ of the light beam shaper satisfies the following formula:

$$\beta = \frac{2\sqrt{2\pi}\,\omega_0 y_0}{\lambda d} \geq 40,$$

in which $\omega_0$ is the waist radius of Gauss light beams; $y_0$ is the half width of a shaped spot; $\lambda$ is the wavelength of the incident light beam; and d is a distance from the light beam shaper to a shaping plane.

11. The analytical instrument according to claim 10, wherein
the light beam focusing module comprises a focusing lens module for focusing the light beam in the second direction Y in which the cells flow, wherein a focus point of the focusing lens module is at a center of the irradiated area, and the focusing lens module comprises at least two cylindrical lenses for compressing and magnifying the light beam in the third direction X that is perpendicular to both the second direction Y in which the cells flow and the first direction Z in which the light beam spreads.

12. The analytical instrument according to claim 11, wherein
the light beam focusing module forms an irradiated area in the flow chamber, and the irradiated area is equal in size to the cell diameter in the second direction Y in which the cells flow.

13. A method for using an irradiation unit for a flow-cytometry-based analytical instrument, comprising:
using a light source for emitting an illuminating light beam in a first direction Z;
causing a light beam focusing module for focusing the illuminating light beam on an irradiated area, wherein the irradiated area comprises an area through which cells to be detected flow in a second direction Y; and
flattening, by disposing a light beam shaper between the light source and the light beam module, distribution of light intensity on the irradiated area along the second direction Y, in which the cells to be detected flow, wherein
the act of flattening the distribution of the light intensity flattens the distribution of the light intensity along the second direction Y but not along the first direction X and
the light beam shaper is further configured for broadening the distribution of the light intensity in the second direction Y to expand a size of the irradiation area in the second direction Y to become larger than an original size of an original irradiation area that is irradiated by the light beam without the light beam shaper.

14. The method of claim 13, wherein the act of causing the light beam focusing module for focusing the illuminating light beam on the irradiated area comprises:
focusing the light beam in the third direction X on the irradiated area; and
focusing the light beam in the second direction Y on the irradiated area.

15. The method of claim 13, further comprising:
adjusting the light beam focusing module or the light beam shaper to approximate a dimension of the irradiated area to a size of one of the cells to be directed.

16. The method of claim 13, further comprising:
adjusting the light beam focusing module or the light beam shaper such that a ratio of a light distribution width in the third direction X and a light distribution width in the second direction Y of the irradiated area comprises a range of 20:1 to 40:1.

17. The method of claim 13, wherein the act of flattening the distribution of the light intensity comprises:
adjusting the light beam focusing module or the light beam shaper to increase a distribution width of the light beam in the third direction X in the irradiated area.

18. The method of claim 13, wherein the act of flattening the distribution of the light intensity comprises:
adjusting the light beam focusing module or the light beam shaper to decrease a distribution width of the light beam in the second direction Y in the irradiated area.

19. The method of claim 13, wherein the act of flattening the distribution of the light intensity comprises:
using the light beam shaper to obtain at least one scattering signal and at least one fluorescent signal having substantially same intensity for a plurality of same cells which are to be detected and enter the irradiated area from a plurality of positions.

20. The method of claim 19, wherein the act of using the light beam shaper comprises:
adjusting a first distribution width in the second direction Y in the irradiated area based at least in part upon a size of a particle to be detected; and
adjusting a second distribution width in the third direction X in the irradiated area to obtain a desired ratio between the first distribution width and the second distribution ratio.

* * * * *